(12) United States Patent
Minamitani (10) Patent No.: US 11,029,273 B2
(45) Date of Patent: Jun. 8, 2021

(54) CORROSION MONITORING DEVICE

(71) Applicant: HITACHI, LTD., Tokyo (JP)

(72) Inventor: Rintarou Minamitani, Tokyo (JP)

(73) Assignee: HITACHI, LTD., Tokyo (JP)

(*) Notice: Subject to any disclaimer, the term of this patent is extended or adjusted under 35 U.S.C. 154(b) by 124 days.

(21) Appl. No.: 16/461,662

(22) PCT Filed: Oct. 23, 2017

(86) PCT No.: PCT/JP2017/038201
§ 371 (c)(1),
(2) Date: May 16, 2019

(87) PCT Pub. No.: WO2018/092519
PCT Pub. Date: May 24, 2018

(65) Prior Publication Data
US 2019/0353608 A1   Nov. 21, 2019

(30) Foreign Application Priority Data
Nov. 18, 2016   (JP) .............................. JP2016-225394

(51) Int. Cl.
*G01N 27/20* (2006.01)
*G01N 33/2045* (2019.01)

(52) U.S. Cl.
CPC ......... *G01N 27/20* (2013.01); *G01N 33/2045* (2019.01)

(58) Field of Classification Search
CPC .... G01N 27/20; G01N 33/2045; G01N 17/02; G01N 17/00; G01N 27/04
USPC .................. 324/700, 699, 693, 691, 600
See application file for complete search history.

(56) References Cited

U.S. PATENT DOCUMENTS

| | | | |
|---|---|---|---|
| 5,015,355 A * | 5/1991 | Schiessl | G01N 17/02 204/404 |
| 2011/0175633 A1 * | 7/2011 | Dobashi | G01M 5/0025 324/700 |
| 2011/0187395 A1 | 8/2011 | Morgan et al. | |

(Continued)

FOREIGN PATENT DOCUMENTS

| | | |
|---|---|---|
| CN | 103226129 A | 7/2013 |
| JP | 2009-150806 A | 7/2009 |

(Continued)

OTHER PUBLICATIONS

International Search Report dated Nov. 28, 2017 for the International PCT Application No. PCT/JP2017/038201.

(Continued)

*Primary Examiner* — Giovanni Astacio-Oquendo
(74) *Attorney, Agent, or Firm* — Volpe Koenig (57) ABSTRACT

A corrosion monitoring device includes: a sensor unit that includes an insulating substrate, a stainless steel plate disposed on the insulating substrate and is configured of stainless steel, an aluminum piece joined to the stainless steel plate and configured of aluminum having a lower corrosion potential than the stainless steel and smaller electrical resistivity than the stainless steel, and extraction electrodes coupled to the stainless steel plate; and an ohm meter that measures an electrical resistance of the sensor unit when a current flows in the sensor unit.

7 Claims, 9 Drawing Sheets

(56) References Cited

U.S. PATENT DOCUMENTS

| | | | | |
|---|---|---|---|---|
| 2012/0043981 A1* | 2/2012 | Chiang | ................... | G01N 17/02 |
| | | | | 324/700 |
| 2012/0176148 A1* | 7/2012 | Chey | ...................... | G01N 27/04 |
| | | | | 324/700 |
| 2014/0159751 A1* | 6/2014 | Hihara | ................... | G01N 17/04 |
| | | | | 324/700 |
| 2014/0190239 A1 | 7/2014 | Minamitani | | |
| 2016/0076989 A1* | 3/2016 | Taskar | ................... | H01L 22/10 |
| | | | | 324/700 |

FOREIGN PATENT DOCUMENTS

| | | |
|---|---|---|
| JP | 5488755 B1 | 5/2014 |
| WO | 2009/141639 A1 | 11/2009 |
| WO | 2013/042179 A1 | 3/2013 |

OTHER PUBLICATIONS

Chinese Office Action dated Mar. 1, 2021 for Chinese Patent Application No. 201780071207.X.

\* cited by examiner

COUNT OF DISSIPATED ALUMINUM PIECES 2 (WORKING EXAMPLE)
COUNT OF CORROSION PITS 11 (COMPARATIVE EXAMPLE)

CORROSION MONITORING DEVICE

TECHNICAL FIELD

The present invention relates to a corrosion monitoring device that targets interior and exterior environments where an electrical and electronic device is installed to monitor a degree of corrosion of metal caused by an attachment of salt content and dust that exist in the environment.

BACKGROUND ART

The electrical and electronic device requires reliability over a long period of time in order to stably operate a target device. In order to provide an increased speed and save a space, many electrical and electronic devices employ a high-density mounting structure and include many electrical and electronic parts formed of a micro-wire structure and a thin film plate structure. In these electrical and electronic parts, salt content and dust deposit are generated due to a long period of usage. On metal surfaces of the electrical and electronic parts where the salt content and the dust attach, an amount of water absorption increases and an electrical conductivity increases compared with a surface without the attachment, and thus, corrosion easily progresses. Such corrosion progress changes an electric property and a magnetic property, and thus, failure and malfunction of the electrical and electronic parts easily occur.

Amount of deposited salt content and dust differs by an installation environment (for example, installation site, timing of use, and period of use) of the electrical and electronic parts. That is, a degree of progress of the corrosion on the metal surface largely differs by the installation environment of the electrical and electronic parts. Therefore, in order to design anti-corrosion measures corresponding to a degree of environmental corrosivity and reflect the anti-corrosion measures to maintenance, it is required to continue evaluating corrosivity of the installation environment of the electrical and electronic device in an easy, short spanned, accurate way over a long period of time.

Relating to such a technique, there is known a technique described in Patent Literature 1. Patent Literature 1 describes a contamination monitoring device that monitors a degree of contamination of a monitoring target installed in a predetermined environment. The contamination monitoring device includes a first electrode portion, a second electrode portion, a current measuring unit, a comparison unit, and a determination unit. The first electrode portion includes two electrodes and a humidity-sensitive material across the two electrodes. The second electrode portion includes other two electrodes and another humidity-sensitive material across the other two electrodes. The current measuring unit measures each of a first current flowing between the two electrodes and a second current flowing between the other two electrodes. The comparison unit compares a measurement result of the first current and a measurement result of the second current. The determination unit determines and monitors a degree of the contamination based on the comparison result. The first electrode portion is installed at a first place having a humidity condition similar to that of the predetermined environment. The second electrode portion is installed at a second place having an environment that has a humidity condition similar to that of the first place and is regarded as there is no contamination.

CITATION LIST

Patent Literature

Patent Literature 1: Japanese Patent No. 5488755

SUMMARY OF INVENTION

Technical Problem

In the contamination monitoring device described in Patent Literature 1, a humidity-sensitive film formed of a polymer resin is used. However, the installation environment (in particular, humidity in air) varies from hour to hour. Accordingly, in association with the use of the contamination monitoring device described in Patent Literature 1, the environment (that is, humidity in air that contacts humidity-sensitive film) for the humidity-sensitive film also varies from hour to hour. Therefore, the humidity-sensitive film easily deteriorates when being exposed in a highly humid environment over a long period of time, and an output current in the contamination monitoring device varies in association with the deterioration of the humidity-sensitive film. That is, even if it is in an identical environment, its output currents differ from immediately after a start of installation to after a lapse of a several months to a several years, and therefore, corrosion cannot be accurately evaluated. Therefore, the technique described in Patent Literature 1 has a problem that a long period of use is difficult.

As described above, the deterioration of the humidity-sensitive film possibly increases the output current. Then, depending on the humidity in the environment, it is possible to have the output current that is determined that a corrosion possibility is high, despite the environment is supposed to be low in corrosion possibility. In view of this, there is a possibility that an evaluation of the corrosion possibility, that is, a responsivity with high accuracy cannot be obtained.

The present invention has been made in view of such a problem, and the problem to be solved by the present invention is to provide a corrosion monitoring device that ensures improved durability and responsivity compared with a conventional one.

Solution to Problem

The inventor has completed the present invention by finding the following perception found by making intensive studies to solve the problem. That is, the gist of the present invention relates to a corrosion monitoring device that includes: a sensor unit that includes an insulating substrate, a first metal layer disposed on the insulating substrate and is configured of a first metal, a second metal layer joined to the first metal layer and is configured of a second metal having a lower corrosion potential than the first metal and smaller electrical resistivity than the first metal layer, and a pair of electrodes coupled to the first metal layer; and a resistance measurement device that measures an electrical resistance of the sensor unit when a current flows between the pair of electrodes.

Advantageous Effects of Invention

According to the present invention, a corrosion monitoring device that ensures improved durability and responsivity compared with a conventional one can be provided.

DESCRIPTION OF EMBODIMENTS

The following describes a configuration (this embodiment) to execute the present invention with reference to the drawings as necessary. First, for convenience of description, a corrosion monitoring device of a comparative example will be described, and next, a corrosion monitoring device of a working example (corrosion monitoring device of this embodiment) will be described comparing with the corrosion monitoring device of the comparative example. An identical member is attached by an identical reference numeral, thus omitting its detailed description.

Figure 15:
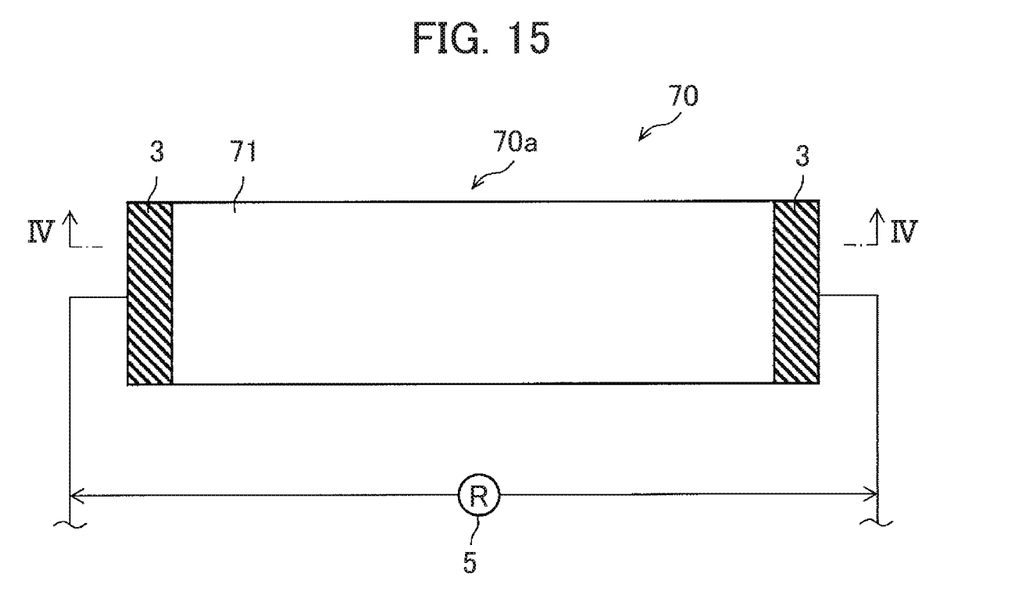
FIG. 15 is a top view of a corrosion monitoring device according to the comparative example.
Figure 16:
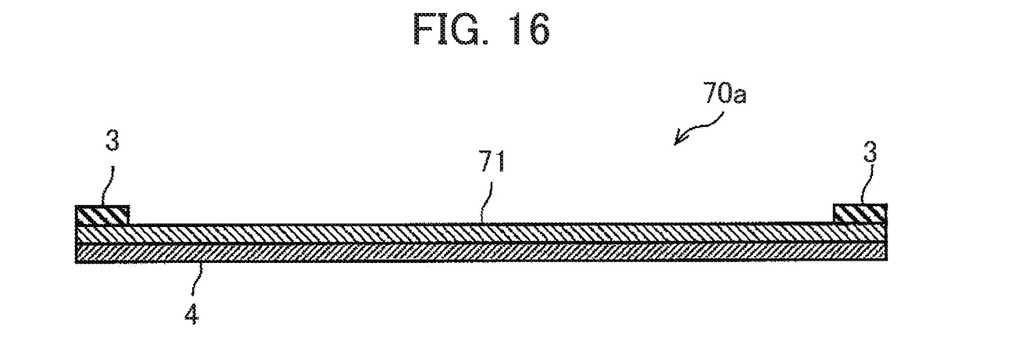
FIG. 16 is an end view of a line IV-IV in FIG. 15.

FIG. 15 is a top view of a corrosion monitoring device 70 of the comparative example. FIG. 16 is an end view taken along a line IV-IV in FIG. 15. The corrosion monitoring device 70 includes a copperplate 71 in a thin film subjected to corrosion is laminated on an insulating substrate 4 configured of an insulating material. The insulating substrate 4 and the copper plate 71 are both in an elongated shape. The copperplate 71 has a top surface that includes a pair of extraction electrodes 3 and 3 at both ends in a longitudinal direction. The insulating substrate 4, the copper plate 71, and the extraction electrodes 3 and 3 configure a sensor unit 70a that detects corrosion (rust) of the copper plate 71.

The extraction electrodes 3 and 3 are coupled to an ohm meter 5 and a power supply unit (not illustrated). The ohmmeter 5 measures an electrical resistance between the extraction electrodes 3 and 3 when a direct current or an alternating current (for example, around a few mA) flows between the extraction electrodes 3 and 3 from this power supply unit. Although illustration is omitted, the extraction electrodes 3 and 3 have external surfaces on which a protective coat configured of, for example, a silicone resin, a urethane resin, and an epoxy resin is formed in order to prevent the corrosion.

Copper chloride and copper oxide obtained by corroding (that is, chlorinating or oxidizing) the copper configuring the copper plate 71 have a large electrical resistance (what is called, insulator). Therefore, the ohm meter 5 measures an electrical resistance change between the extraction electrodes 3 and 3 that occurs due to the generation of such copper chloride and copper oxide on the surface of the copper plate 71.

In the corrosion monitoring device 70 illustrated in FIG. 15, an amount of corrosion is measured based on an electric resistance value that increases in association with the copper plate 71 subjected to corrosion corrodes. That is, the study by the inventor has found that there was a correlation between an amount of change in an electric resistance value, and an attached amount of airborne salt content and dust and an amount of corrosion of the copper plate 71. Therefore, based on this amount of change in the electric resistance value, the attached amount of salt content and dust and the amount of corrosion of the copper plate 71 can be evaluated. Specifically, for example, the environmental corrosivity can be diagnosed in accordance with ISO 11844-1.

Here, a description will be given of corrosion of a metal plate caused by a salt content with reference to FIG. 17.

Figure 17A:
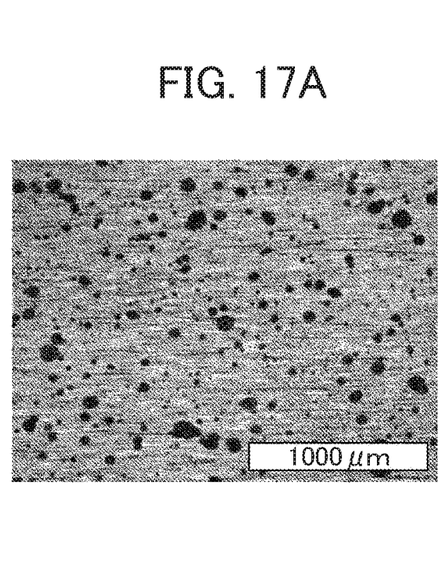
FIG. 17 includes drawing substitute photographs illustrating a state of corrosion of a metal plate caused by a salt content, and the view on the right side is a ten-time enlarged view of the view on the left side.
Figure 17B:
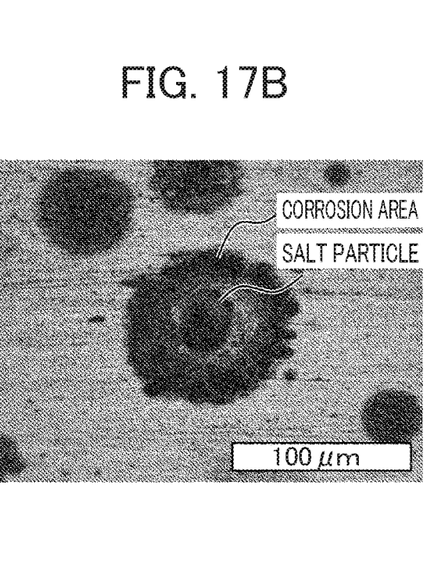

FIG. 17 includes drawing substitute photographs illustrating a state of corrosion of a metal plate caused by a salt content. The view on the right side is a ten-time enlarged view of the view on the left side. The metal plate used in this FIG. 17 is a copper plate. FIG. 17 illustrates salt particles (equivalent to a salt content 6 described later) formed on a surface of the copper plate and corrosion areas (equivalent to a corrosion pit 11 illustrated in FIG. 18 described later) occurred in peripheral areas of the salt particles. In the view on the right side in FIG. 17, the salt particle is approximately in a circular shape in a top view, and the corrosion area is approximately in a circular ring shape such that the corrosion area surrounds the salt particle in a top view. As illustrated in the view on the right side in FIG. 17, the salt particles of a several 10 μm in diameter are attached at intervals of approximately 50 μm to 100 μm, and the salt particles deliquesce to form the corrosion areas under water films around the salt particles.

Figure 18:
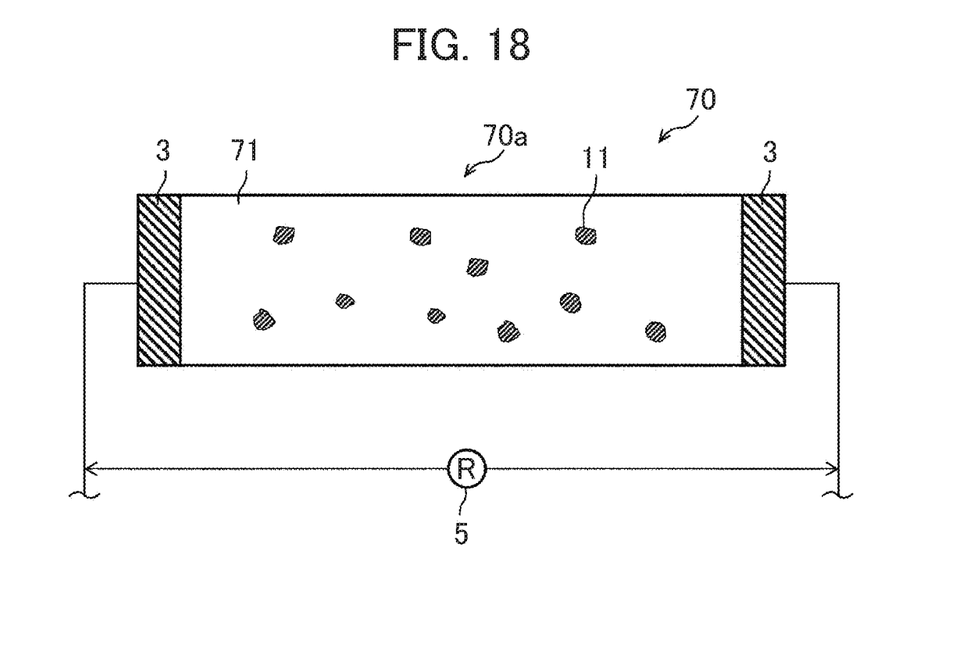
FIG. 18 is a view illustrating a state of corrosion pits occurred on a surface of a copper plate configuring the corrosion monitoring device of the comparative example.

FIG. 18 is a view illustrating a state of the corrosion pits 11 occurred on the surface of the copperplate 71 configuring the corrosion monitoring device 70 of the comparative example. When the corrosion monitoring device 70 is exposed in an environment where the salt content and the dust float in the air, the salt content and the dust attach to the copper plate 71 configuring the corrosion monitoring device 70 (more specifically, the sensor unit 70a). At this time, the salt content and the dust are considered to attach at intervals of approximately 50 µm to 100 µm as described with reference to FIG. 17 described above. Therefore, the corrosion pits 11 as the corrosion areas occurring on the surface of the copperplate 71 are also considered to occur at intervals of approximately 50 µm to 100 µm.

In the corrosion monitoring device 70, the degree of corrosion is monitored (evaluated) based on a change in the electric resistance value that increases as the copper plate 71 subjected to corrosion uniformly corrodes. Therefore, as illustrated in FIG. 18, a sensitivity of the electric resistance value is low for a local defect such as the corrosion pit 11 that locally occurs, and thus, it is difficult to accurately monitor local corrosion caused by the salt content and the dust. In particular, while details will be described later with reference to FIG. 6, according to the study by the inventor, it is considered that the change in the electric resistance value is slight and a response sensitivity is not good even though a cross-sectional area decreases due to a local formation of the corrosion pits 11 as illustrated in FIG. 18. Therefore, the inventor has studied about a corrosion monitoring device excellent in durability and also excellent in responsivity.

Figure 1:
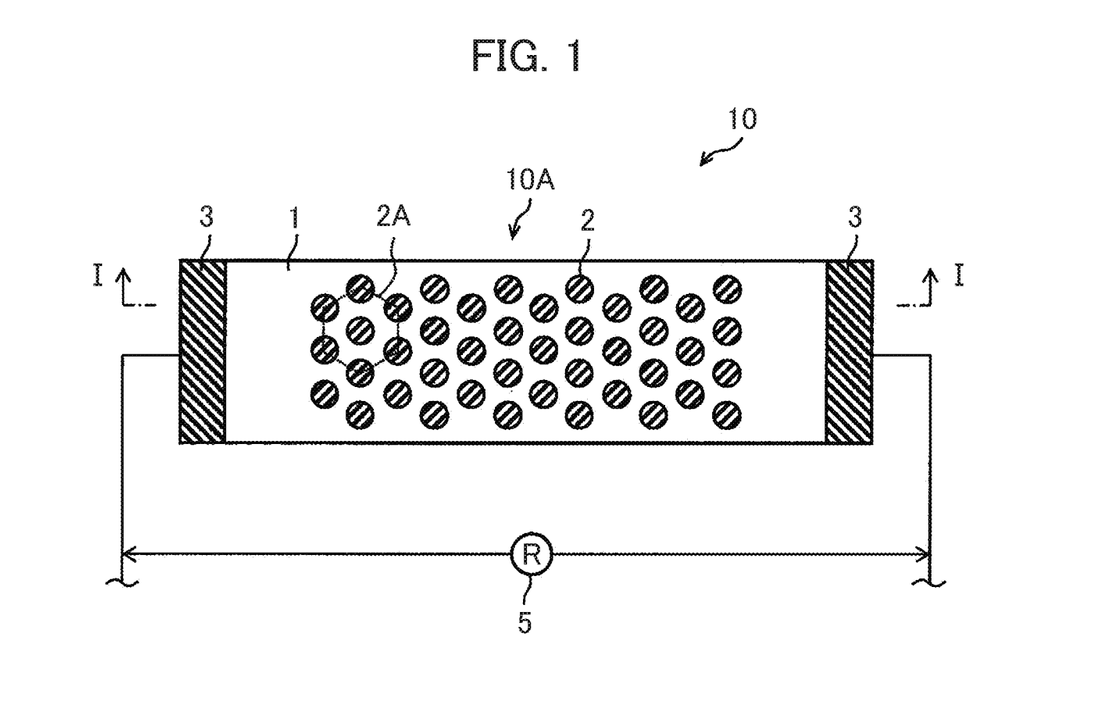
FIG. 1 is a top view of a corrosion monitoring device according to a first embodiment.
Figure 2:
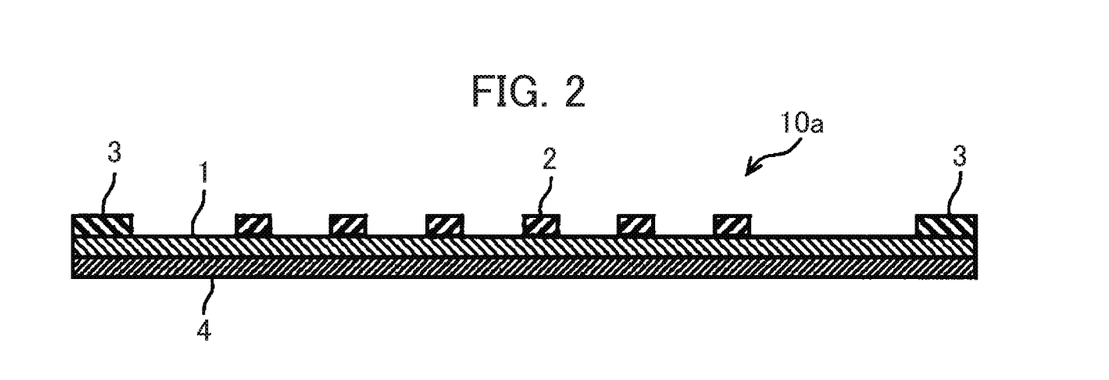
FIG. 2 is an end view taken along a line I-I in FIG. 1.

FIG. 1 is a top view of a corrosion monitoring device 10 of a first embodiment. FIG. 2 is an end view taken along a line I-I in FIG. 1. In the corrosion monitoring device 10, similarly to the corrosion monitoring device 70 described above, the ohm meter 5 (resistance measurement device) measures an electrical resistance between the extraction electrodes 3 and 3 coupled to a stainless steel plate 1. However, in the corrosion monitoring device 10 illustrated in FIG. 1, the insulating substrate 4 has a surface on which the flat plate shaped stainless (SUS, stainless steel, first metal) plate 1 is joined (laminated). The stainless steel plate 1 has a surface on which a plurality of aluminum (second metal) pieces 2 in a circular shape in a top view are sparsely joined (laminated). That is, a sensor unit 10a configuring the corrosion monitoring device 10 is configured by including the stainless steel plate 1, the aluminum piece 2, the extraction electrodes 3 and 3, and the insulating substrate 4.

Forming the aluminum piece 2 into a circular shape easily makes a thickness of the aluminum piece 2 uniform when the aluminum piece 2 is joined to the stainless steel plate 1. Therefore, the aluminum piece 2 easily corrodes uniformly when the aluminum 2 corrodes, and thus, local corrosion of the aluminum piece 2 is prevented. Irrespective of a corrosion position of the dust and the salt content, a contact portion of a water film 7 (will be described later) to the aluminum piece 2 is a part of a circle (circular arc) configuring an outer periphery of the aluminum piece 2. Therefore, irrespective of a corrosion position of the dust and the salt content, the degree of progress of the corrosion is identical, and the local corrosion of the aluminum piece 2 is prevented in this respect too.

The plurality of aluminum pieces 2 are joined such that the adjacent aluminum pieces 2 are positioned at respective apexes of a regular hexagon 2A. This ensures equalizing an interval between the adjacent aluminum pieces 2. Therefore, irrespective of an attached position of the dust and the salt content, it is possible to easily corrode each of the aluminum pieces 2 in a particularly similar mode.

The aluminum piece 2 has a thickness of, for example, approximately 10 µm or less, preferably, approximately 1 µm or less. The circular shaped aluminum piece 2 has a size of, for example, approximately 50 µm to 100 µm in diameter. Furthermore, the interval between the adjacent aluminum pieces 2 is, for example, approximately 50 µm to 100 µm. For the stainless steel plate 1, a plate material may be used, or, for example, sputtering, deposition, and plating can join the stainless steel plate 1 on a surface of the insulating substrate 4. The aluminum piece 2 can be joined on a surface of the stainless steel plate 1 by, for example, sputtering, deposition, and plating.

While the details are described later, when corrosivities of the stainless steel and the aluminum are compared, the stainless steel (first metal) is hard to corrode (corrosion potential is high) and the aluminum (second metal) is easy to corrode (corrosion potential is low). In the corrosion monitoring device 10, using the corrosivity of the aluminum piece 2 compared with that of the stainless steel plate 1, configuring the sensor unit 10a, the degree of corrosion of the metal is evaluated.

Figure 3:
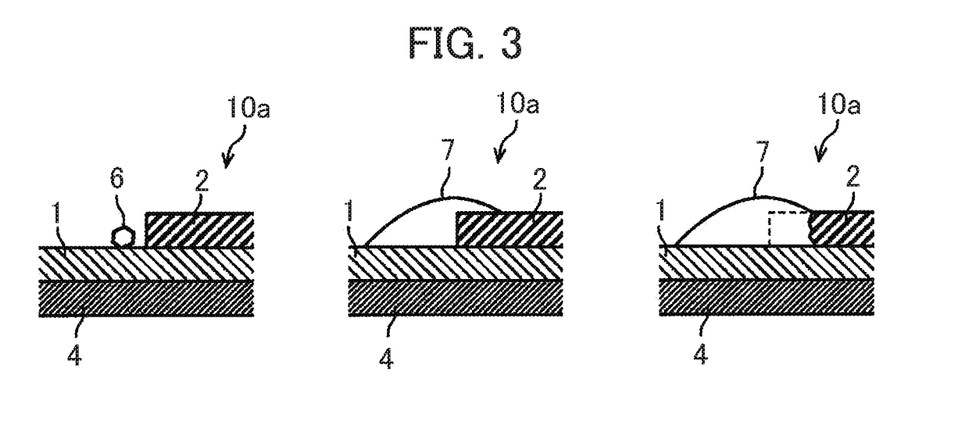
FIG. 3 includes views illustrating states where corrosion progresses when a salt content attaches to the corrosion monitoring device according to the first embodiment. The view on the left side is a view illustrating a state immediately after the salt content attaches. The view in the center is a view illustrating a state when a water film formed by a deliquescence of the attached salt content cross-links a stainless steel plate and an aluminum piece. The view on the right side is a view illustrating a state when the cross-linked water film has caused progress of corrosion (dissolution) of the aluminum piece.

FIG. 3 includes views illustrating states where corrosion of the aluminum piece 2 progresses when the salt content 6 attaches to the corrosion monitoring device 10 (more specifically, the sensor unit 10a) according to the first embodiment. The view on the left side is a view illustrating a state immediately after the salt content 6 attaches. The view in the center is a view illustrating a state when the water film 7 formed by a deliquescence of the attached salt content 6 cross-links the stainless steel plate 1 and the aluminum piece 2. The view on the right side is a view illustrating a state when the cross-linked water film 7 has caused progress of corrosion (dissolution) of the aluminum piece 2. Here, while only the "salt content 6" is illustrated for simplification of the description, the "dust" also has a similar tendency. In the following description, the description for the "dust" is also omitted.

The study by the inventor has found that the surface on which the salt content 6 was attached had a large amount of adsorbed water content compared with that on a clean surface without the attached salt content 6 as described above. This phenomenon is considered to be due to the deliquescence of the salt content 6. Therefore, as illustrated in the view on the left side in FIG. 3, when the salt content 6 attaches to the surface of the stainless steel plate 1, a water content easily attaches to the portion where the salt content 6 is attached. As a result, as illustrated in the view at the center in FIG. 3, the water film 7 is formed so as to be astride the stainless steel plate 1 and the aluminum piece 2.

Here, the aluminum, which configures the aluminum piece 2, easily corrodes as described above compared with the stainless steel, which configures the stainless steel plate 1. Therefore, as illustrated in the view on the right in FIG. 3, the water film 7 formed so as to be astride the stainless steel plate 1 and the aluminum piece 2 progresses corrosion of the aluminum piece 2 as a base metal, which easily corrodes. At this time, corrosion of the stainless steel plate 1 as a noble metal is reduced.

Figure 4:
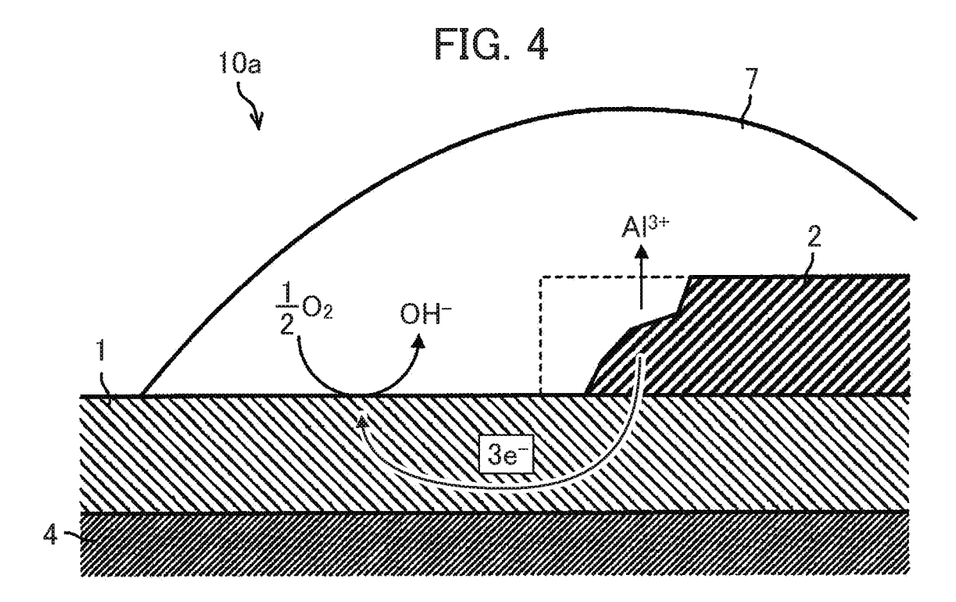
FIG. 4 is a view describing a reaction mechanism that occurs between the stainless steel plate and the aluminum piece.

FIG. 4 is a view describing a reaction mechanism that occurs between the stainless steel plate 1 and the aluminum piece 2. In FIG. 4, a part of the chemical formula is omitted from the illustration for simplification of the description. When the water film 7 is formed so as to stride across the stainless steel plate 1 on a side of the noble metal less likely to corrode and the aluminum piece 2 on a side of the base metal that easily corrodes, the following respective reactions are caused on the stainless steel plate 1 and the aluminum piece 2.

Specifically, as illustrated in FIG. 4, on the aluminum piece 2 on a lower potential side, an anode reaction (metal dissolution reaction: $Al \rightarrow Al^{3+} + 3e^-$) occurs. This dissolves the aluminum piece 2 in the water film 7. Then, electrons generated here move to the stainless steel plate 1 joined to the aluminum piece 2. Then, on the stainless steel plate 1 on a higher potential side, a cathode reaction (reduction reaction of dissolved oxygen: $1/2.O_2+H_2O+2e^- \rightarrow 2OH^-$) occurs using the electrons generated on the aluminum piece 2. Therefore, what is called, a galvanic current flows between the stainless steel plate 1 and the aluminum piece 2.

The corrosion caused by bringing different metals into contact thus progresses with the anode (oxidation reaction) and the cathode (reduction reaction) being positionally separated. The galvanic current concentrates near an interface between the stainless steel plate 1 and the aluminum piece 2. Therefore, as illustrated in FIG. 4, the corrosion progresses from the left side of the aluminum piece 2 toward the right side. Then, after the whole aluminum piece 2 corrodes, a corrosion reaction of the stainless steel plate 1 progresses alone. The stainless steel plate 1 is metal less likely to corrode, and moreover, even though it corrodes, the corrosion pits 11 (see FIG. 18 described above) localize. Therefore, the change in the electric resistance value caused by the formation of the corrosion pits 11 is negligible.

Figure 5:
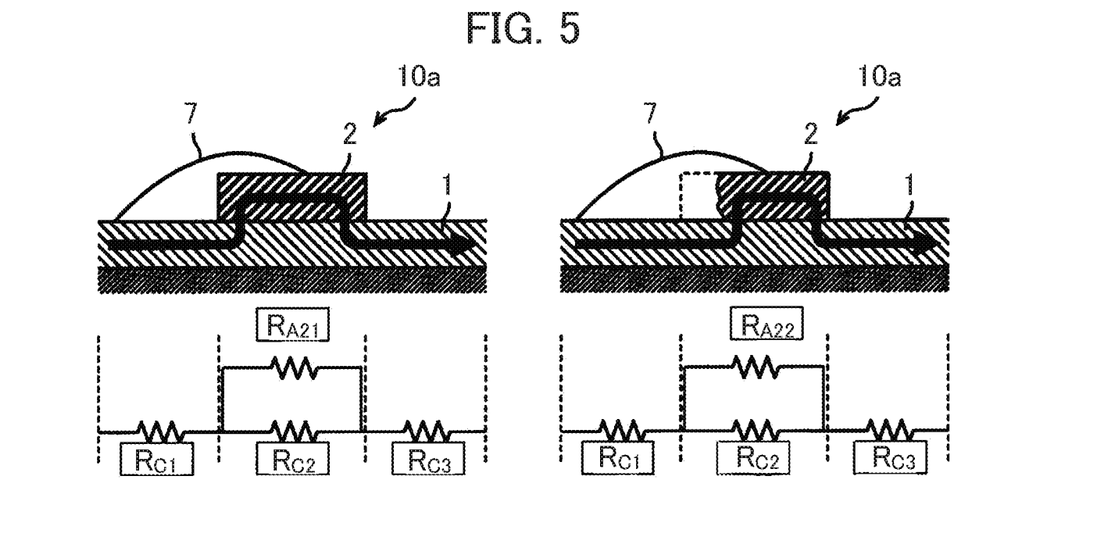
FIG. 5 includes views illustrating a change in an equivalent circuit of electrical resistors before and after the aluminum piece dissolves.

FIG. 5 includes views illustrating a change in an equivalent circuit of electrical resistors before and after the aluminum piece 2 dissolves. This FIG. 5 is to describe a measurement principle by the corrosion monitoring device 10 according to the first embodiment. While the details will be described later with reference to FIG. 7, electrical resistivity of the aluminum (second metal) is smaller than electrical resistivity of the stainless steel (first metal). That is, the stainless steel has a low electrical conductivity compared with that of the aluminum. Therefore, in the view on the left side in FIG. 5, when a current flows between the extraction electrodes 3 and 3 (see FIG. 1), the current flows to the aluminum 2 more preferentially than to the stainless steel plate 1 in the portion where the stainless steel 1 and the aluminum 2 are joined (bold arrow in view on left side in FIG. 5).

Schematically illustrating this phenomenon by the equivalent circuit makes it possible to consider that the portion of the stainless steel plate 1 on which the aluminum piece 2 is not joined is coupled to resistors $R_{C1}$ and $R_{C3}$ as illustrated in the lower portion of the view on the left side in FIG. 5. Meanwhile, it is possible to consider that, in the joint portion between the stainless steel plate 1 and the aluminum piece 2, a resistor $R_{C2}$ is coupled in parallel in the portion of the stainless steel plate 1 and a resistor $R_{A21}$ is coupled in parallel in the portion of the aluminum piece 2, since there is electrical resistivity difference between the stainless steel and the aluminum as described above. At this time, $R_{C2} > R_{A21}$ is satisfied. The resistance value $R_0$ of the sensor unit 10a measured by the ohm meter 5 (see FIG. 1) becomes $R_0 = R_{C1} + R_{A21} \cdot R_{C2}/(R_{A21}+R_{C2}) + R_{C3}$.

When the corrosion progresses (that is, dissolution of the aluminum piece 2 progresses) by the mechanism illustrated in FIG. 4 described above, a conductive path in the aluminum piece 2 shortens and a conductive path in the stainless steel plate 1 with an electrical resistance larger than that of the aluminum piece 2 lengthens (see view on right side in FIG. 5) compared prior to the corrosion progresses (see view on left side in FIG. 5). Therefore, the conductive path with small electrical resistivity shortens, and thus, the electrical resistance increases. Specifically, the resistance $R_{A21}$ in the portion where the aluminum piece 2 originally existed increases to a resistance $R_{A22}$. The resistance value $R_1$ of the sensor unit 10a measured by the ohm meter 5 (see FIG. 1) becomes $R_1 = R_{C1} + R_{A22} \cdot R_{C2}/(R_{A22}+R_{C2}) + R_{C3}$.

As described above, in the corrosion monitoring device 10 according to the first embodiment, the whole resistance increases from $R_0$ to $R_1$ by the dissolution of the aluminum piece 2. Such a resistance change continuously occurs as the dissolution of the aluminum piece 2 progresses. Therefore, in the corrosion monitoring device 10 according to the first embodiment, monitoring the whole resistance change (increase) monitors the dissolution of the aluminum piece 2, that is, the degree of corrosion of the metal. Since the electrical resistance immediately changes by the dissolution of the aluminum piece 2, the corrosion monitoring device 10 is excellent in responsivity to the corrosion (this will be described again with reference to FIG. 6).

The environment where the corrosion monitoring device 10 is installed is predictable to some extent, and therefore, the corrosivity of the metal is also predictable to some extent. Therefore, increasing a count of the aluminum piece 2, thickening the thickness of the aluminum piece 2, and increasing the size of the aluminum piece 2 depending on the installation site of the corrosion monitoring device 10 ensures causing the dissolution of the aluminum piece 2 over a long period of time, and thus, the durability can be improved.

Figure 6:
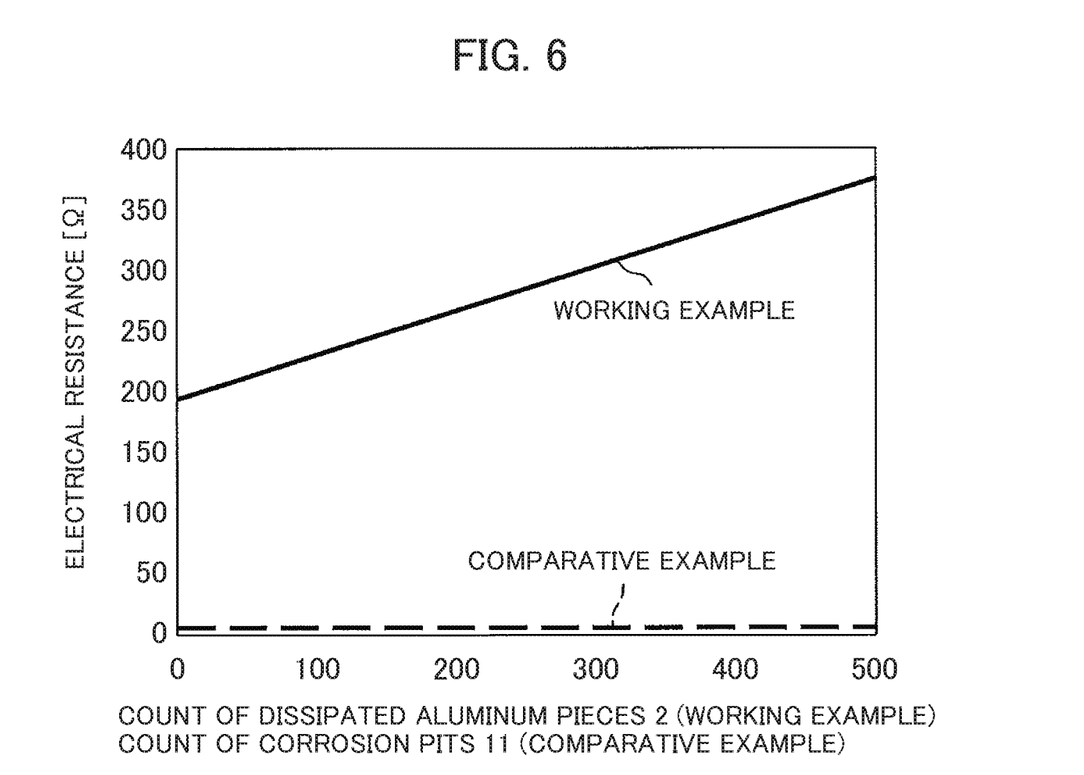
FIG. 6 is a graph showing relations between a count of dissipated aluminum pieces and a count of corrosion pits, and an electrical resistance in the corrosion monitoring device in a working example and a corrosion monitoring device in a comparative example.

FIG. 6 is a graph showing relations between a count of the dissipated aluminum piece 2 and a count of the corrosion pit count 11 (see FIG. 18), and the electrical resistance in the corrosion monitoring device of the working example (the corrosion monitoring device 10 illustrated in FIG. 1) and the corrosion monitoring device of the comparative example (the corrosion monitoring device 70 illustrated in FIG. 15). As the stainless steel plate 1 and the copper plate 71 used in the corrosion monitoring devices 10 and 70, ones with a width of 1 mm×a length of 25 mm×a thickness of 100 nm were used. The aluminum piece 2 used in the corrosion monitoring device 10 had a size of 50 μm in diameter×100 nm in thickness, and five hundred of the aluminum pieces 2 were disposed at intervals of 50 μm. FIG. 6 has graphed resistance values measured by the ohmmeter 5 after continuously flowing a current of 5 mA to each of these corrosion monitoring devices 10 and 70.

As illustrated in this FIG. 6, in the corrosion monitoring device (the corrosion monitoring device 10 illustrated in FIG. 1) of the working example, as the corrosion progressed, that is, as the count of the dissipated aluminum pieces 2 increased, a magnitude of a resistance measured by the ohm meter 5 has also increased. However, in the corrosion monitoring device in the comparative example (the corrosion monitoring device 70 illustrated in FIG. 15), even though the count of the corrosion pits 11 increased, the resistance measured by the ohm meter 5 has hardly changed. This is considered that the resistance change has hardly occurred since a sufficient cross-sectional area (conductive path) was ensured even though the corrosion pits 11 were formed as the result of the corrosion pits 11 progressed on the whole surface of the stainless steel plate 1. Accordingly, it has been found that, with the corrosion monitoring device 10 according to the first embodiment, the corrosion monitoring device with excellent durability and responsivity can be provided.

Figure 7:
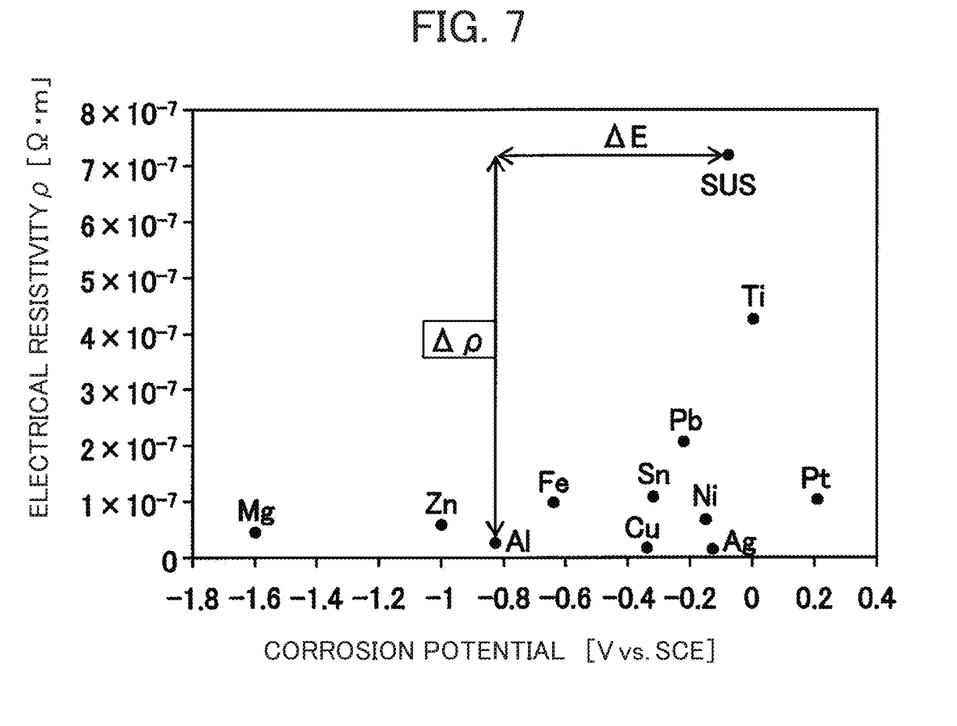
FIG. 7 is a graph showing a relation between a corrosion potential and electrical resistivity in seawater.

FIG. 7 is a graph (plot) showing a relation between a corrosion potential and electrical resistivity in seawater. The corrosion potential indicated on a horizontal axis in FIG. 7 is about a saturated calomel electrode (SCE) as a reference electrode. In this description, for simplification of the description, the corrosion potential in a water solution in which a salt content has deliquesced/dissolved is not shown. The relation between the corrosion potential about the water solution in which the salt content has deliquesced/dissolved and electrical resistivity also has a tendency similar to the tendency shown in FIG. 7.

As described above, in the corrosion monitoring device 10 according to the first embodiment, a stainless steel (the stainless steel plate 1) is used as metal less likely to corrode and an aluminum (the aluminum piece 2) is used as metal that easily corrodes. However, for a combination of usable metals, it is not limited to such a combination, and can be appropriately selected, for example, based on the graph in FIG. 7.

However, as the metal that causes the cathode reaction described with reference to FIG. 4 (metal usable instead of stainless steel described above. Hereinafter, referred to as "first metal"), the metal with a relatively high corrosion potential (less likely to corrode) and with large electrical resistivity is preferred. Meanwhile, as the metal that causes the anode reaction described with reference to FIG. 4 (metal usable instead of aluminum described above. Hereinafter, referred to as "second metal"), the metal with a relatively low corrosion potential (easily corrodes) and with relatively small electrical resistivity is preferred. Therefore, it is preferred to use these metals in combination. Applying this to FIG. 7, when one first metal is selected, it is preferred to use metal approximately on a lower left viewed from the plot of the first metal as the second metal.

Here, an electrical resistivity difference $\Delta\rho$ between the first metal and the second metal is preferred to be large. The large $\Delta\rho$ ensures increasing the resistance change when the second metal dissolves (corrodes) to ensure enhanced responsivity. An electric potential difference $\Delta E$ between corrosion potentials of the first metal and the second metal is preferred to be large from an aspect of enhancing the responsivity by reducing as much corrosion of the first metal as possible and promoting as much corrosion of the second metal as possible. When $\Delta E$ is too large, the corrosion of the second metal excessively progresses to easily lower durability. Therefore, in such a case, the durability can be improved by, for example, thickening the thickness and increasing the size of the second metal. In order to improve the durability, an interval between the adjacent second metals (for example, aluminum piece 2) may be broadened.

As described above, the corrosion monitoring device 10 according to the first embodiment, in particular, the change in the electrical resistance in the sensor unit 10*a* depends on, for example, the corrosion potential difference $\Delta E$ between the first metal and the second metal, the electrical resistivity difference $\Delta\rho$ between the first metal and the second metal, the shape of the second metal (including, for example, size and thickness), and the interval between the adjacent second metal pieces. However, some types of metal are large in resistance change by the temperature (that is, some has temperature coefficient of resistance that largely changes by temperature). Therefore, in particular, as the first metal whose corrosion is reduced is preferred to have a small temperature coefficient of resistance. However, even the one with a large temperature coefficient of resistance can monitor the corrosion with high accuracy by additionally using a thermometer and correcting a measured resistance corresponding to the temperature measured by the thermometer.

Based on these points, the second metal subjected to corrosion is preferred to be at least one of iron, copper, zinc, and magnesium, as well as the aluminum described above. The first metal whose corrosion is reduced as much as possible is preferred to be at least one of nickel and chrome as well as the stainless steel (SUS) described above, considering that metal with a small temperature coefficient of resistance is preferred. While the chrome is not shown in FIG. 7, the chrome presents electrical resistivity of a degree similar to that of lead, and presents a corrosion potential of a degree similar to those of the stainless steel (SUS) and the nickel. It is preferred to combine one certain first metal with the second metal positioned at approximately lower left viewed from the plot of the first metal (for example, combining stainless steel (SUS) with aluminum) out of these preferable examples of the first metal and the second metal by applying to FIG. 7, and use them.

Figure 8:
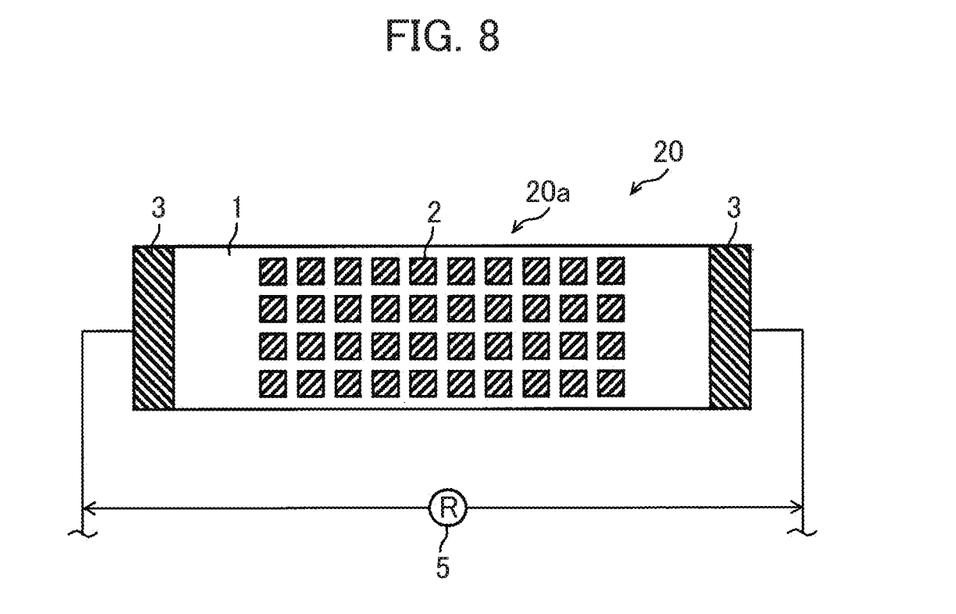
FIG. 8 is a top view of a corrosion monitoring device according to a second embodiment.

FIG. 8 is a top view of a corrosion monitoring device 20 according to a second embodiment. The corrosion monitoring device 20 illustrated in FIG. 8 is unlike the corrosion monitoring device 10, a size of the aluminum piece 2 is in a rectangular shape (square shape). However, other configurations than that are identical to that of the corrosion monitoring device 10 described above and a sensor unit 20*a* is configured by including these rectangular shaped aluminum pieces 2. A side of the aluminum piece 2 is, for example, approximately 50 μm to 100 μm. Then, the intervals between the adjacent aluminum pieces 2 are at regular intervals (for example, approximately 50 μm to 100 μm).

Forming the shape of the aluminum piece 2 into a square shape ensures joining more aluminum pieces 2 on the surface of the stainless steel plate 1 compared with the circular-shaped aluminum plate 8. This ensures further enhanced durability of the corrosion monitoring device 20.

Figure 9:
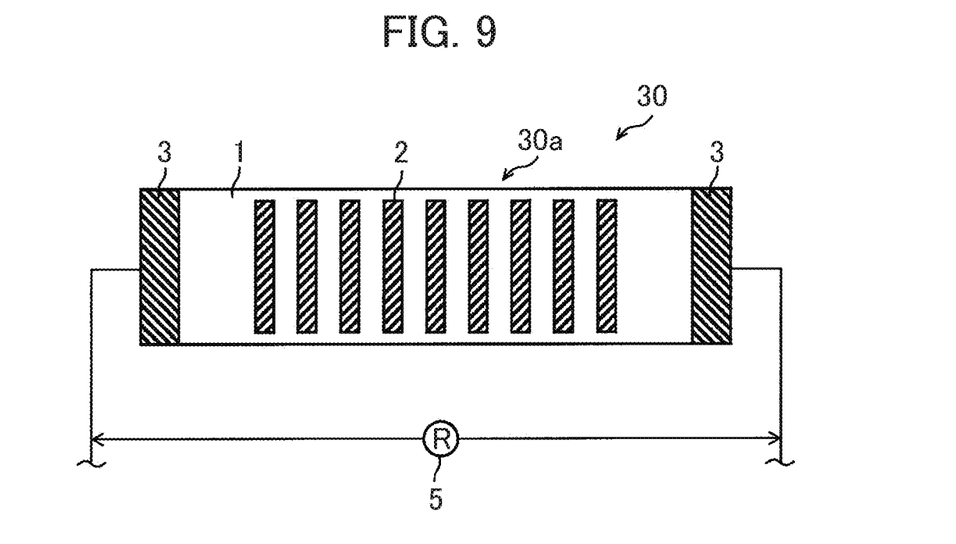
FIG. 9 is a top view of a corrosion monitoring device according to a third embodiment.

FIG. 9 is a top view of a corrosion monitoring device 30 according to a third embodiment. In the corrosion monitoring device 30 illustrated in FIG. 9, a plurality of the rectangular shaped aluminum pieces 2 are joined in a direction perpendicular to a flow direction of current (right-left direction on paper surface in FIG. 9). However, other configurations than that are identical to that of the corrosion monitoring device 10 described above and a sensor unit 30*a* is configured by including these rectangular shaped aluminum pieces 2. This ensures the increased size of the aluminum piece 2 compared with the ones of the corrosion monitoring devices 10 and 20 described above, and the corrosion of the aluminum piece 2 progresses over a long period of time. Therefore, the resistance change can be continuously monitored over a long period of time and can improve durability of the corrosion monitoring device 30.

A count of the joined aluminum pieces 2 can be increased while a large area of the aluminum piece 2 is ensured. This causes the aluminum piece 2 to continue corroding due to the corrosion of the remaining aluminum pieces 2 even if one aluminum piece 2 locally corrodes. This ensures monitoring the resistance change and with this respect as well, the durability of the corrosion monitoring device 30 can be improved.

Figure 10:
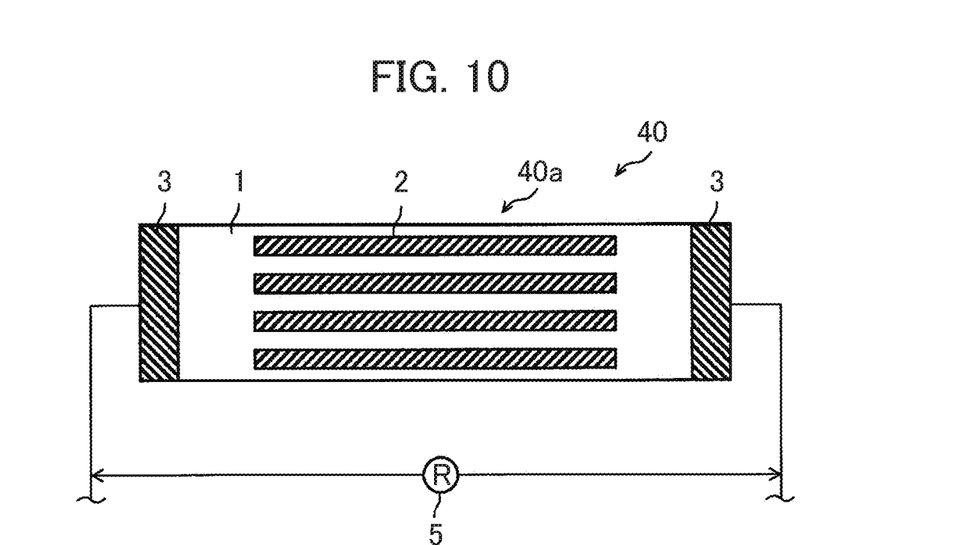
FIG. 10 is a top view of a corrosion monitoring device according to a fourth embodiment.

FIG. 10 is a top view of a corrosion monitoring device 40 according to a fourth embodiment. In the corrosion monitoring device 40 illustrated in FIG. 10, the plurality of rectangular shaped aluminum pieces 2 are joined in a direction identical to the flow direction of current (right-left direction on paper surface in FIG. 9). However, other configurations than that are identical to the corrosion monitoring device 10 described above and a sensor unit 40*a* is configured by including these rectangular shaped aluminum pieces 2. This ensures the increased size of the aluminum piece 2 compared with the ones of the corrosion monitoring devices 10 and 20 described above, similarly to the corrosion monitoring device 30 described above, and ensures improved durability of the corrosion monitoring device 40.

For example, when corrosion locally occurs, there may be a case where a middle of the aluminum piece 2 elongated in the flow direction of current is cut off. This largely increases the electrical resistance, which has been decreased by being disposed in the flow direction of current. In such a case, it is considered that the environment where the corrosion monitoring device 40 is installed is an environment in which local corrosion easily occurs. The local corrosion in the electrical and electronic device particularly causes a breakdown of the electrical and electronic device. Therefore, detecting a high possibility of such local corrosion at an early stage ensures reducing the breakdown of the electrical and electronic device at the early stage.

Figure 11:
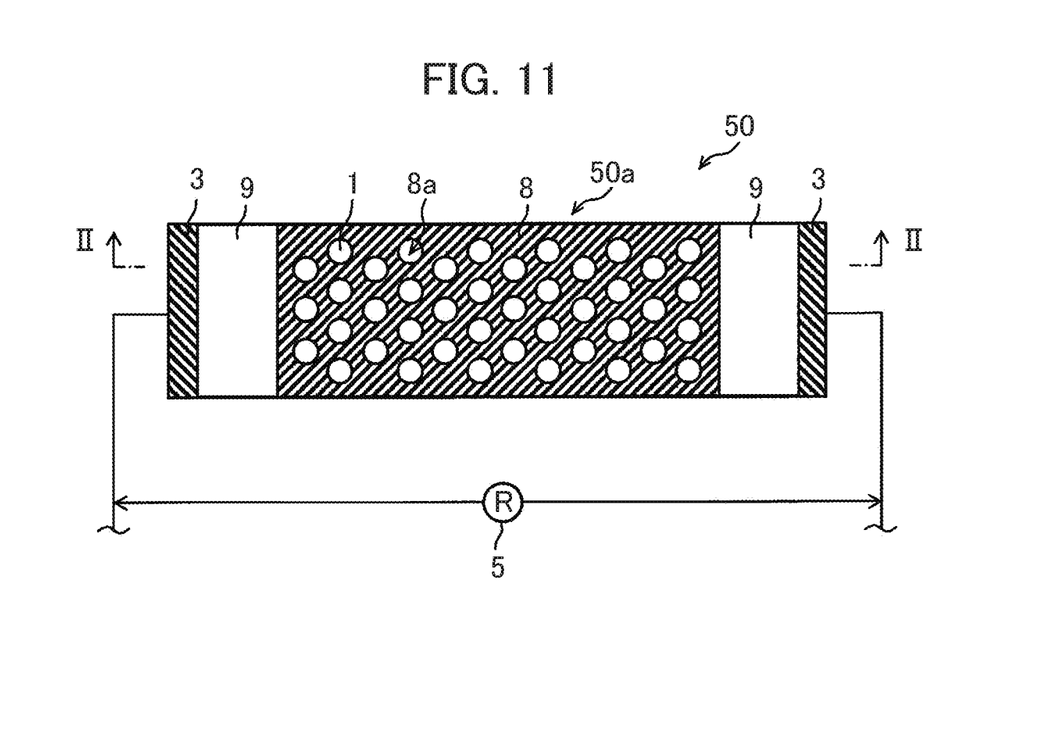
FIG. 11 is a top view of a corrosion monitoring device according to a fifth embodiment.
Figure 12:
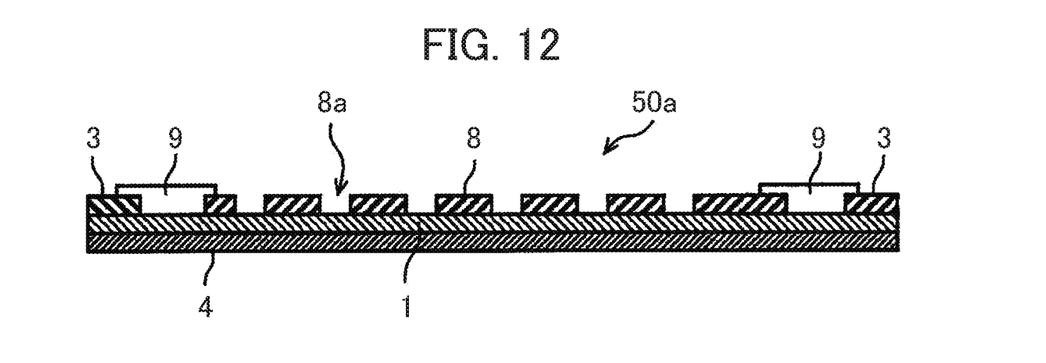
FIG. 12 is an end view taken along a line II-II in FIG. 11.

FIG. 11 is a top view of a corrosion monitoring device 50 according to a fifth embodiment. FIG. 12 is an end view taken along a line II-II in FIG. 11. In each of the embodiments described above, the plurality of aluminum pieces 2 are joined on the surface of the stainless steel plate 1. However, in the corrosion monitoring device 50 illustrated in FIG. 11 and FIG. 12, the stainless steel plate 1 and the aluminum plate 8 having a plurality of circular shaped through-holes 8a are joined (laminated) on the insulating substrate 4. That is, the stainless steel plate 1 is laminated on the insulating substrate 4 and the aluminum plate 8 is laminated on the surface of the stainless steel plate 1. This through-hole 8a has a size identical to the size of the aluminum piece 2 described above. Furthermore, these through-holes 8a are disposed so as to be at positions of the respective apexes of the regular hexagon, similarly to the regular hexagon 2A, with reference to FIG. 1 described above.

In a portion that is not covered with an aluminum plate 8 on the surface of the stainless steel plate 1, a film 9 configured of, for example, a silicone resin, a urethane resin, and an epoxy resin, is formed in order to be moisture-proof and gas-proof. Accordingly, in the corrosion monitoring device 50, a sensor unit 50a is configured by including the stainless steel plate 1, the aluminum plate 8 having the through-holes 8a, the insulating substrate 4, and the extraction electrodes 3 and 3, and the film 9.

In this corrosion monitoring device 50, the surface of the stainless steel plate 1 is exposed to the outside through the through-holes 8a in the top view. Viewing from the aluminum plate 8 joined on the surface of this stainless steel plate 1, this portion of the through-hole 8a is depressed. Therefore, the water film 7 (not illustrated in FIG. 11 and FIG. 12) easily accumulates in this portion of the through-hole 8a. Therefore, the water film 7 easily contacts both the stainless steel configuring the stainless steel plate 1 and the aluminum configuring the aluminum plate 8, and thus, the reaction described with reference to FIG. 4 described above can be promoted.

Compared with each of the embodiments described above, the aluminum plate 8 as the metal subjected to corrosion has an extremely large volume. Therefore, the corrosion of the metal can be monitored particularly over a long period of time. Furthermore, since a joined area between the stainless steel plate 1 and the aluminum plate 8 is wide, the adhesion strength of the aluminum plate 8 is high. Therefore, a delamination of the aluminum plate 8 can be sufficiently prevented to ensure enhanced durability.

Figure 13:
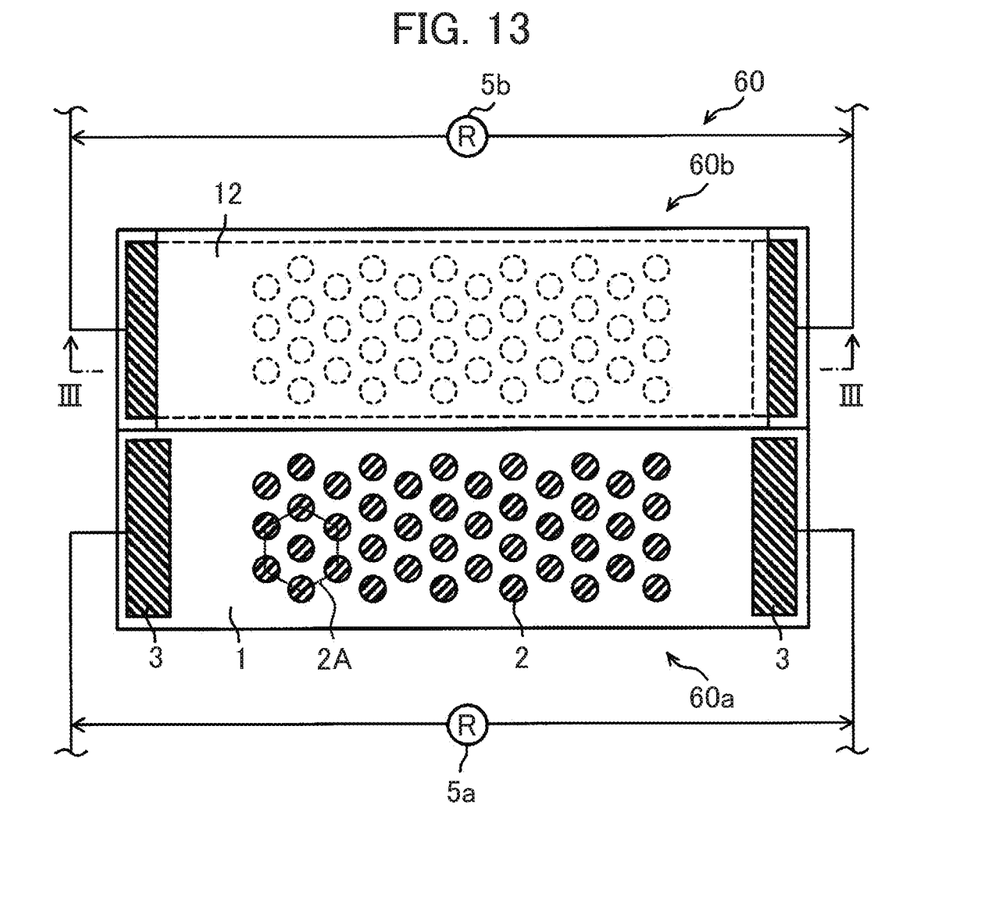
FIG. 13 is a top view of a corrosion monitoring device according to a sixth embodiment.
Figure 14:
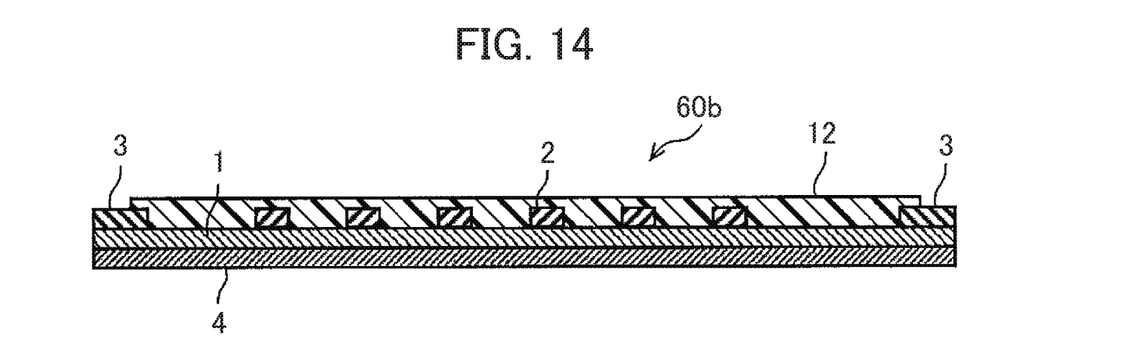
FIG. 14 is an end view taken along a line III-III in FIG. 13.

FIG. 13 is a top view of a corrosion monitoring device 60 according to a sixth embodiment. FIG. 14 is an end view taken along a line III-III in FIG. 13. The corrosion monitoring device 60 illustrated in FIG. 13 and FIG. 14 includes a sensor unit 60a and a reference sensor unit 60b. The sensor unit 60a includes the stainless steel plate 1 and the aluminum piece 2 subjected to corrosion. The reference sensor unit 60b similarly includes the stainless steel plate 1 and the aluminum piece 2 but do not corrode.

Among these, the sensor unit 60a has a configuration similar to that of the sensor unit 10a illustrated in FIG. 1 described above. An ohmmeter 5a measures the electrical resistance when the current flows. Meanwhile, the reference sensor unit 60b includes a film 12 formed so as to cover the stainless steel plate 1 and the aluminum piece 2 configuring the sensor unit 10a (see FIG. 1) described above. Then, an ohm meter 5b measures the electrical resistance when the current flows. The film 12 is formed in order to be moisture-proof and gas-proof, and configured of, for example, a silicone resin, a urethane resin, and an epoxy resin.

As described above, the temperature sometimes changes the resistance of the metal. Therefore, in the corrosion monitoring device 60 illustrated in FIG. 13 and FIG. 14, the corrosion of the metal is monitored considering such a temperature change. Specifically, evaluating a difference between the resistance value in the corrosion monitoring device 60a and the resistance value in the corrosion monitoring device 60b ensures monitoring the corrosion of the metal considering the temperature. This ensures monitoring the metal corrosion with higher accuracy.

While the present invention has been described with six embodiments, the present invention is not limited by the examples described above. For example, the embodiments described above can be appropriately combined and executed. It is also possible to execute after applying various kinds of deformation.

For example, in the embodiments described above, the stainless steel plate 1 as metal less likely to corrode is joined on the surface of the insulating substrate 4, and the aluminum piece 2 and the aluminum plate 8 that easily corrode are joined on the surface of the stainless steel plate 1 in this order. However, a joining order (lamination order) of the stainless steel plate 1, and the aluminum piece 2 and the aluminum plate 8 may be inversed. That is, for example, the insulating substrate 4, the aluminum plate 8, and the stainless steel plate 1 having the through-holes may be joined in this order. However, in this case, the extraction electrodes 3 and 3 described above are coupled to the stainless steel plate 1.

LIST OF REFERENCE SIGNS 1 stainless steel plate (first metal layer)
2 aluminum piece (second metal layer)
3 extraction electrode (pair of electrodes)
4 insulating substrate
5 ohm meter (resistance measurement device)
5a ohm meter (resistance measurement device)
5b ohm meter (resistance measurement device)
6 salt content
7 water film formed by salt content deliquescing
8 aluminum plate (second metal layer)
9 film
10 corrosion monitoring device
10a sensor unit
11 corrosion pit
12 film
20 corrosion monitoring device
20a sensor unit
30 corrosion monitoring device
30a sensor unit
40 corrosion monitoring device
40a sensor unit
50 corrosion monitoring device
50a sensor unit
60 corrosion monitoring device
60a sensor unit
60b reference sensor unit (sensor unit)

The invention claimed is:

1. A corrosion monitoring device comprising:
   at least one sensor unit that includes:
      an insulating substrate;
      a first metal layer disposed on the insulating substrate, the first metal layer being configured of a first metal;
      a second metal layer joined to the first metal layer, the second metal layer being configured of a second metal having a lower corrosion potential than the first metal and smaller electrical resistivity than the first metal layer; and
      a pair of electrodes coupled to the first metal layer; and
   a resistance measurement device that measures an electrical resistance of the at least one sensor unit when a current flows between the pair of electrodes.

2. The corrosion monitoring device according to claim 1, wherein the insulating substrate, the first metal layer, and the second metal layer are joined in this order.

3. The corrosion monitoring device according to claim 1, wherein the first metal layer is in a flat plate shape, and the second metal layer is in a circular shape in a top view, the second metal layer being sparsely joined to the first metal layer on a surface of the first metal layer.

4. The corrosion monitoring device according to claim 3, wherein a plurality of the second metal layers are joined so as to be positioned at respective apexes configuring a regular hexagon on a surface of the first metal layer.

5. The corrosion monitoring device according to claim 1,
   wherein two of each of the at least one sensor units and the resistance measurement devices are provided,
   one sensor unit of the at least one sensor units has a film formed in order to reduce corrosion of the first metal layer and the plurality of second metal layers so as to cover the first metal layer and the plurality of second metal layers.

6. The corrosion monitoring device according to claim 1,
   wherein the first metal is at least one of stainless steel, nickel, and chrome, and
   the second metal is at least one of iron, aluminum, copper, zinc, and magnesium.

7. The corrosion monitoring device according to claim 1, wherein the insulating substrate, the second metal layer, and the first metal layer are joined in this order.

* * * * *